United States Patent
Arnold et al.

(10) Patent No.: US 7,271,381 B2
(45) Date of Patent: Sep. 18, 2007

(54) DEVICE TO DETECT INDIVIDUAL MOVING OBJECTS HAVING VERY SMALL DIMENSIONS

(75) Inventors: Martin Arnold, Huefingen (DE); Norbert Irmer, Villingen-Schwenningen (DE); Hubert Schill, Elzach (DE); Markus Heinzler, Thalheim (DE)

(73) Assignee: Minebea Co., Ltd., Nagano-ken (JP)

( * ) Notice: Subject to any disclaimer, the term of this patent is extended or adjusted under 35 U.S.C. 154(b) by 90 days.

(21) Appl. No.: 10/918,890

(22) Filed: Aug. 16, 2004

(65) Prior Publication Data

US 2005/0058387 A1   Mar. 17, 2005

(30) Foreign Application Priority Data

Aug. 19, 2003 (DE) ................. 103 38 108

(51) Int. Cl.
*G01J 1/04* (2006.01)
*H03F 3/08* (2006.01)
*G02B 6/00* (2006.01)
*G02B 6/12* (2006.01)
*G01N 21/00* (2006.01)

(52) U.S. Cl. .................... 250/227.11; 250/214 A; 385/12; 385/14; 356/442

(58) Field of Classification Search ............... 250/221, 250/222.1, 573–577, 227.11–227.14, 339.07, 250/339.11, 339.12, 227.28, 214 A, 214 LS; 356/336, 343, 436, 442; 385/9, 12, 14, 31, 385/39, 42

See application file for complete search history.

(56) References Cited

U.S. PATENT DOCUMENTS 4,255,754 A   3/1981   Crean et al.

(Continued)

FOREIGN PATENT DOCUMENTS

DE   201 04 248   6/2001

(Continued)

OTHER PUBLICATIONS

U.S. Appl. No. 11/029,924, Martin et al, Device to Detect and/or Characterize Individual Moving Objects Having Very Small Dimensions, filed Jan. 5, 2005.

*Primary Examiner*—Georgia Epps
*Assistant Examiner*—Don Williams
(74) *Attorney, Agent, or Firm*—Baker & Daniels LLP

(57) ABSTRACT

The invention relates to a device to detect individual moving objects having very small dimensions. The device according to the invention comprises a photo electric sensor having at least one light beam transmitter and one light beam receiver, the objects that are to be measured moving through the optical path of the photo electric sensor, a first bundle of optical waveguides whose inputs are connected to the light beam transmitter and whose outputs are arranged in a row alongside each other, the light beams emitted by the outputs forming the optical path of the photo electric sensor, a second bundle of optical waveguides which are arranged in a row alongside each other whose inputs pick up the light beams emitted by the first bundle of optical waveguides and whose outputs are connected to the light beam receiver, and an evaluation unit which is coupled to the light beam transmitter and the light beam receiver and which registers a change in the received light intensity of the photo electric sensor produced by the objects passing through the optical path.

17 Claims, 2 Drawing Sheets

U.S. PATENT DOCUMENTS

| | | | |
|---|---|---|---|
| 4,329,591 A | * | 5/1982 | Fujiwara et al. ............. 250/548 |
| 4,827,143 A | * | 5/1989 | Munakata et al. .......... 250/574 |
| 6,075,239 A | * | 6/2000 | Aksyuk et al. ............. 250/229 |
| 2002/0047633 A1 | | 4/2002 | Jurs et al. |
| 2003/0071197 A1 | * | 4/2003 | Sugiyama ............... 250/214 A |

FOREIGN PATENT DOCUMENTS

| | | |
|---|---|---|
| DE | 100 33 077 | 1/2002 |
| DE | 43 34 785 | 4/2003 |
| DE | 203 04 211 | 7/2003 |
| JP | 55-125408 | 9/1980 |
| JP | 55-164336 | 12/1980 |
| JP | 64-87320 | 3/1989 |
| JP | 1-158990 | 11/1989 |
| WO | WO81/01200 | 4/1981 |

\* cited by examiner

DEVICE TO DETECT INDIVIDUAL MOVING OBJECTS HAVING VERY SMALL DIMENSIONS

BACKGROUND OF THE INVENTION

The invention relates to a device to detect individual moving objects having very small dimensions, particular dimensions in the sub-mm range.

Photo electric sensors are frequently used to detect moving objects. The measurement volumes of photo electric sensors without additional beam-forming optics that are available on the market are too large, that is, the diameter of the optical path is too large to detect very small individual objects with a high repeat rate and with short object spacing. Beam-forming optics that could remedy this problem need a large installation space compared to the very small objects. If there is only a restricted installation space available, these kinds of photo electric sensors cannot be employed.

Existing evaluation electronics analyze the changes in the signal when an object passes through and thus recognizes the objects. Particularly in the case of very small objects, however, environmental influences, electrical disturbances and transit phenomena result in faulty detection since the signal picked up by the light beam receiver is very small compared to the interfering signals. These kinds of evaluation circuits do not produce a counting result that is sufficiently reliable in order to count, for example, drops of liquid that have a diameter of 200 μm or less.

SUMMARY OF THE INVENTION

The object of the invention is to provide a device to detect individual moving objects having very small dimensions which is capable of detecting and analyzing a change in the light signals caused by the passing objects in such a way that each individual through moving object can be reliably recognized.

The device according to the invention comprises a photo electric sensor having at least one light beam transmitter and one light beam receiver, the objects that are to be measured moving through the optical path of the photo electric sensor, a first bundle of optical waveguides whose inputs are connected to the light beam transmitter and whose outputs are arranged in a row alongside each other, the light beams emitted by the outputs forming the optical path of the photo electric sensor, a second bundle of optical waveguides which are arranged in a row alongside each other whose inputs pick up the light beams emitted by the first bundle of optical waveguides and whose outputs are connected to the light beam receiver, and an evaluation unit which is coupled to the light beam transmitter and the light beam receiver and which registers a change in the received light intensity of the photo electric sensor produced by the objects passing through the optical path.

In accordance with one form of the invention, to detect the small objects both the very small mechanical dimensions as well as the optical coupling characteristics of the optical waveguides are exploited. The mechanical dimensions of the optical waveguides are in the order of magnitude of the objects that are to be measured which means that additional beam-forming optical elements to recognize the objects are not required. Moreover, the coupling characteristics of the waveguides when installed, particularly the restricted incoming beam angle typical of optical waveguides, prevent the input of optical interfering signals produced by outside sources of light. To make the optics tolerant to mechanical installation tolerances, several wave guides are arranged in one line. The width of the line in conjunction with its height gives the detection volume.

The detection device described above enables the objects that move through the photo electric sensor to be reliably recognized and/or characterized, taking up very little installation space and being insensitive to interference.

If the optical decoupling and/or coupling characteristics of the waveguides are not sufficient to recognize or characterize the small objects when they pass through the photo electric sensor, the light beam can be additionally conditioned with the aid of fiber-optic components (e.g. GRIN lenses).

In a preferred embodiment of the invention, the optical waveguides of the first bundle and the second bundle are arranged parallel to each other, the outputs of the first bundle of optical waveguides are arranged in a plane with the inputs of the second bundle of optical waveguides and are located opposite them. The optical path of the photo electric sensor takes the approximate shape of a disk whose thickness is within the order of magnitude of the objects that are to be measured, the cross-section of the detection volume in the direction of movement of the objects being significantly smaller than the cross-section transversal to the direction of movement of the objects. The narrow, disk-shaped detection volume produces very good detection sensitivity for small objects following each other at a rapid rate.

In order to additionally increase the detection sensitivity, provision can be made according to the invention for the wavelength of the light emitted by the light beam transmitter to correspond to at least one absorption wavelength of the object. This is particularly advantageous for the detection of liquid objects such as drops of liquid.

In accordance with one form of the invention, the evaluation electronics comprise a first amplifier connected to the light beam receiver, an adder connected to the output of the first amplifier, a second amplifier connected to the output of the adder and a threshold value switch connected to the output of the second amplifier. The output of the threshold value switch is connected to a microprocessor control that has a plurality of analogue and digital inputs and outputs.

The microprocessor control enables the evaluation electronics to be optimally adapted to the operating range of the individual components with the aid of variable amplification factors of the amplifier, a subtraction of offsets, an adjustable switching threshold of the threshold value switch and a variable light intensity of the light beam transmitter. The electronics can be automatically compensated for environmental influences, component aging, soiling of the photo electric sensor etc.

An application-related embodiment of the invention will now be explained in more detail on the basis of the figures. Further characteristics, advantages and applications of the invention can be derived from the drawings and their description.

DESCRIPTION OF A PREFERRED EMBODIMENT OF THE INVENTION

A possible application of the invention could be seen in counting drops of liquid, particularly drops with a diameter in the sub-mm range. Such small drops can be produced by a microdispenser. The microdispenser shoots out drops having a diameter of less than 100 μm from a jet. For many applications, it is necessary to count every single drop that leaves the microdispenser. With a drop speed of approx. 2 m/s and a repeat frequency of 2000 Hz to 4000 Hz, counting the individual drops is made difficult. However, the device according to the invention solves this problem without difficulty.

Figure 1:
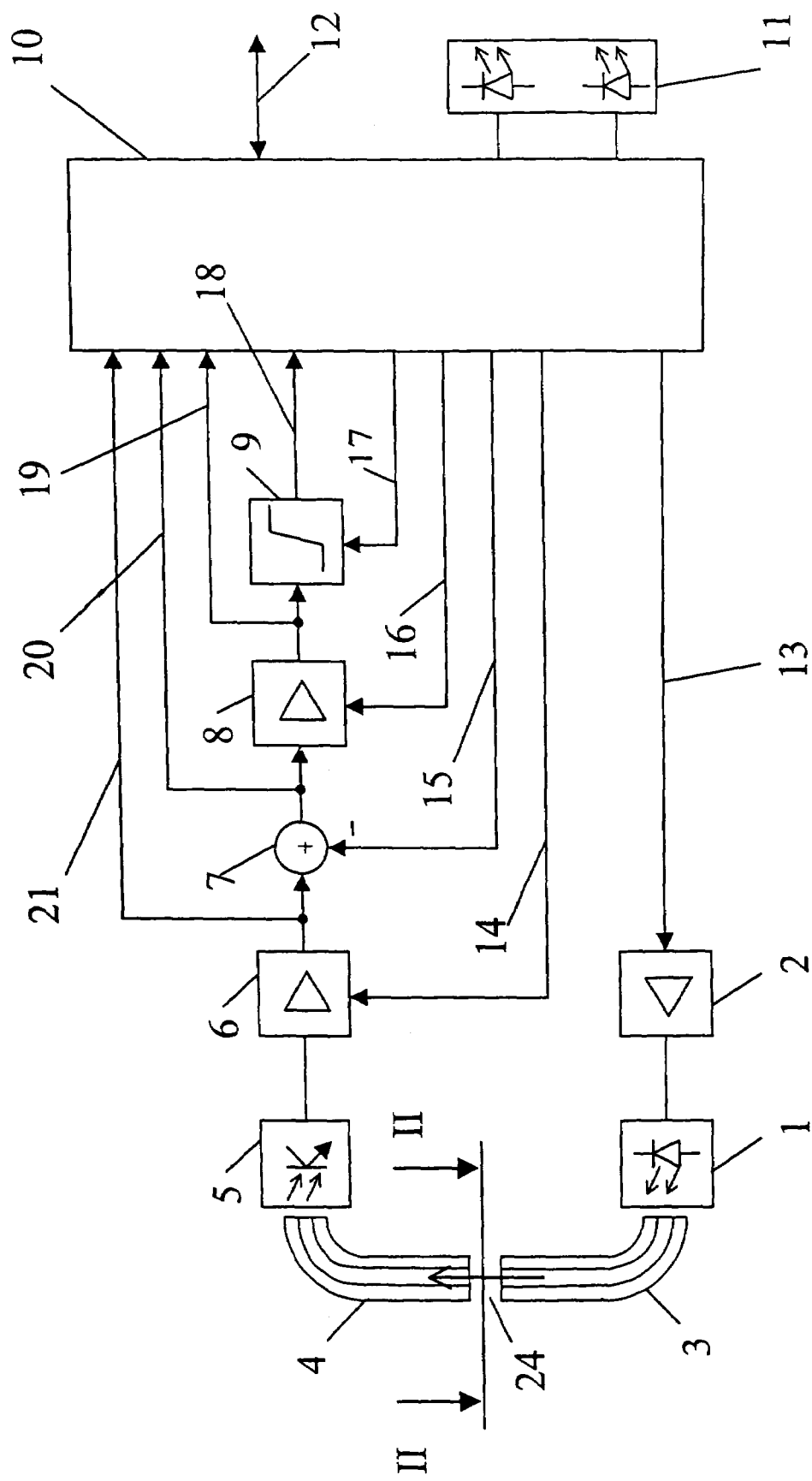
FIG. 1 shows a schematic block diagram of the detection device

As can be seen from FIG. 1, the device comprises a light beam transmitter 1, such as a light-emitting diode or a laser diode that is controlled by a driver 2. The light is fed to a first bundle of optical waveguides 3 whose inputs are connected to the light beam transmitter 1. The input cross-section of the bundle of optical waveguides is adjusted to the cross-section of the light beam transmitter used, e.g. circular. The outputs of the individual optical waveguides 3 are arranged in a row alongside each other and form a flat strip. The light beams emitted by the outputs define the optic path of the photo electric sensor and pass a detection volume 24 through which the objects that are to be detected move.

A second bundle of optical waveguides 4 is located opposite the outputs of the first optical waveguides 3 whose inputs are likewise arranged in a row alongside each other and which pick up light beams emitted by the first bundle of optical wave guides 3. The outputs of the optical waveguides 4 are connected to a light beam receiver 5 which registers the light signals and transforms them into electric signals. A photodiode or photo-transistor can, for example, be used as a light beam receiver 5. A CCD line sensor is also basically suitable for use as a light beam receiver. If a CCD line sensor is used, there is no longer need for the bundle of optical waveguides (4) on the receiver side since the CCD line sensor can be arranged directly opposite the bundle of optical waveguides (3) on the transmitter side. In this case, the device can additionally detect the lateral position of the CCD light beam receiver at which the object crossed the photo electric sensor. For this purpose, an evaluation unit reads the individual receiver fields of the CCD sensor one after the other. The detection speed of CCD sensors has an upper limit due to the maximum read-out speed of the receiver fields.

The above-mentioned evaluation unit is coupled to the light beam transmitter 1 and the light beam receiver 5 and records the change in light intensity produced by the objects passing the optic path. For this purpose, the electrical signal coming from the light beam receiver 5 is amplified in a first amplifier 6. A voltage is subtracted from this amplified signal in an adder 7 whose absolute value approximately corresponds to the direct voltage portion of the signal voltage. The signal is then amplified again in a second amplifier 8. Changes in the signal at the light beam receiver 5 can now be analyzed over the full range of the amplifier 8 since the direct voltage portion has been removed in the adder 7. A switching threshold is then detected using a threshold value switch 9 and the output signal 18 is fed to a counter circuit which takes the form of a microprocessor control 10.

The signals at the outputs of the amplifier 6, the adder 7 and the amplifier 8 are also fed to the microprocessor control via signal lines 21, 20, 19 and analyzed there.

The amplification factors of the amplifiers 6 and 8 can be adjusted, the microprocessor control 10 being able to optimally adjust the amplification factors as a function of the output signals measured via lines 21 and 19. This takes place via signal lines 14 and 16.

Using the output signal 21 of the first amplifier, the microprocessor control can determine the amount of voltage to be supplied to the adder via line 15, which is then subtracted from the signal voltage. The threshold value of the threshold value switch 9 can be adjusted via signal line 17.

Moreover, the light intensity of the light beam transmitter can be controlled by the microprocessor control. At the same time, the driver 2 and thus the current supplied to the light beam transmitter 1 is influenced by line 13.

The microprocessor control 10 is programmed in such a way that, with the aid of the differently designed amplifiers, offsets, thresholds and light beam transmitter currents, the evaluation electronics can be optimally adjusted to the operating range of the individual components. By controlling the light intensity of the light beam transmitter, a moving object can be simulated so that here it is possible to optimally adjust the evaluation electronics to the signal of the light beam receiver and the properties of the photo electric sensor. The adjustment process can be carried out automatically by the microprocessor control so that such environmental influences as temperature, aging, soiling of the photo electric sensor etc. can be continuously compensated.

Figure 2:
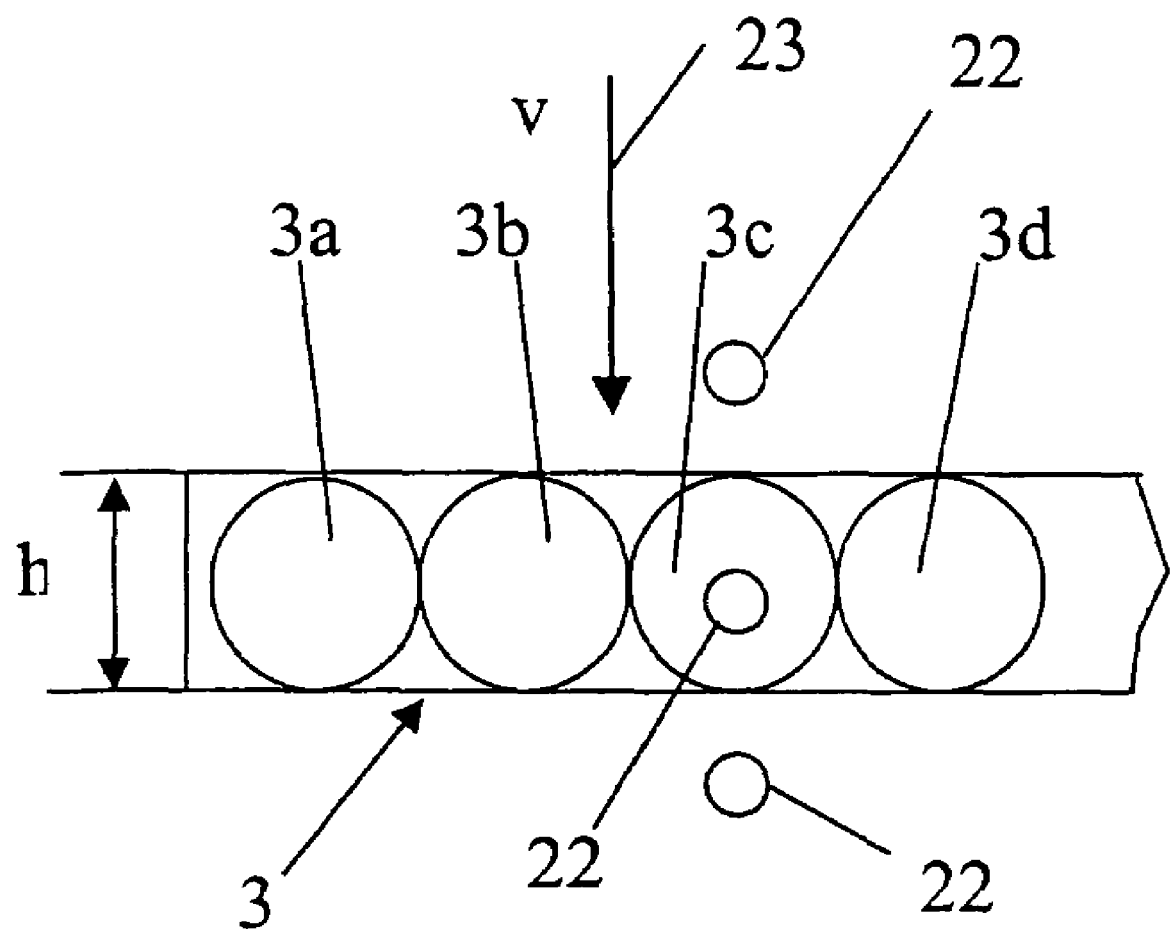
FIG. 2 shows an enlarged view of the optical waveguide of the photo electric sensor according to arrows II in FIG. 1.

An enlarged view from above of the bundle of optical waveguides 3 is shown in FIG. 2. The bundle consists of a row of waveguides 3a, 3b, 3c, 3d, etc. lying alongside each other that form a detection plane with height h. The objects 22 that are to be detected move with speed v in the direction of the arrow 23 through the detection plane.

The detection device with evaluation electronics according to the invention is insensitive to interference, eliminates environmental influences, compensates component tolerances and enables objects moving through the photo electric sensor to be reliably counted.

The invention claimed is:

1. A device to detect individual moving objects having very small dimensions, comprising:
   a photo electric sensor having at least one light beam transmitter and one light beam receiver, objects that are to be measured moving through the optical path of the photo electric sensor, the optical path of the photo electric sensor being shaped like a disk whose thickness (h) is within the order of magnitude of the objects that are to be measured;
   a first bundle of optical waveguides whose inputs are connected to the light beam transmitter and whose outputs are arranged in a row alongside each other, the light beams emitted by the outputs forming the optical path of the photo electric sensor, a second bundle of optical waveguides which are arranged in a row alongside each other whose inputs pick up the light beams emitted by the first bundle of optical waveguides and whose outputs are connected to the light beam receiver, and an evaluation unit which is coupled to the light beam transmitter and the light beam receiver and which registers a change in the received light intensity of the photo electric sensor produced by the objects passing through the optical path;
   the cross-section (h) of the detection volume in the direction of movement of the objects being significantly smaller than the cross-section transverse to the direction of movement of the objects;

wherein the evaluation unit comprises a first amplifier connected to the light beam receiver, an adder connected to the output of the first amplifier, a second amplifier connected to the output of the adder, a threshold value switch connected to the output of the second amplifier and a microprocessor control connected to the threshold value switch.

2. The device according to claim 1, wherein the optical waveguides of the first bundle are arranged parallel to each other.

3. A The device according to claim 1, wherein the optical waveguides of the second bundle are arranged parallel to each other.

4. The device according to claim 2, wherein the outputs of the first bundle of optical waveguides are arranged on one plane with the inputs of the second bundle of optical waveguides and are located opposite them.

5. The device according to claim 1, wherein the optical waveguides of the second bundle are arranged parallel to each other.

6. The device according to claim 1, wherein the outputs of the first bundle of optical waveguides are arranged on one plane with the inputs of the second bundle of optical waveguides and are located opposite them.

7. A The device according to claim 1, wherein the wavelength of the light emitted by the light beam transmitter corresponds to at least one absorption wavelength of the object.

8. The device according to claim 1, wherein the microprocessor control has a plurality of analog inputs and a plurality of digital inputs and outputs.

9. The device according to claim 1, wherein the output of the first amplifier, the output of the adder, the output of the second amplifier and the threshold value switch are each connected to an analog input of the microprocessor control.

10. The device according to claim 1, wherein the first amplifier has an input to control its amplification factor, an output of the microprocessor control being connected to said first amplifier input.

11. The device according to claim 1, wherein the second amplifier has an input to control its amplification factor, an output of the microprocessor control being connected to said second amplifier input.

12. The device according to claim 1, wherein an output of the microprocessor control is connected to an input of the adder.

13. The device according to claim 1, wherein the threshold value switch has an input to control the threshold value, an output of the microprocessor control being connected to said threshold value switch input.

14. The device according t oclaim 1, wherein the combination consisting of the light beam transmitter and a driver for the transmitter has an input to regulate the light intensity, an output of the microprocessor control being connected to the input of said combination.

15. A method to operate a device to detect individual moving objects having very small dimensions comprising a photo electric sensor having at least one light beam transmitter and one light beam receiver, objects that are to be measured moving through the optical path of the photo electric sensor, a first bundle of optical waveguides whose inputs are connected to the light beam transmitter and whose outputs are arranged in a row alongside each other, the light beams emitted by the outputs forming the optical path of the photo electric sensor, a second bundle of optical waveguides which are arranged in a row alongside each other whose inputs pick up the light beams emitted by the first bundle of optical waveguides and whose outputs are connected to the light beam receiver, and an evaluation unit which is coupled to the light beam transmitter and the light beam receiver and which registers a change in the received light intensity of the photo electric sensor produced by the objects passing through the optical path; wherein:

the light emitted from the light beam transmitter is picked up by the light beam receiver, transformed into an electrical signal and fed to a first amplifier where it is amplified;

the signal amplified by the first amplifier is fed to an input of an adder and a direct voltage value determined by a microprocessor control is subtracted there and an output signal is produced;

the output signal of the adder is fed to a second amplifier where it is amplified;

the signal amplified by the second amplifier is fed to an input of a threshold value switch; and an output signal of the threshold value switch is fed to the microprocessor control and analyzed there.

16. The method according to claim 15, wherein the microprocessor control controls amplification factors of the first and second amplifiers in such a way that respective amplified output signals do not exceed a predetermined signal level and/or an available signal level is fully exploited.

17. The method according to claim 16, wherein the microprocessor control controls a threshold value of the threshold value switch in such a way that a change in the signal on the input of the threshold value switch caused by an object can be reliably recognized.

* * * * *

UNITED STATES PATENT AND TRADEMARK OFFICE
CERTIFICATE OF CORRECTION

| | |
|---|---|
| PATENT NO. | : 7,271,381 B2 |
| APPLICATION NO. | : 10/918,890 |
| DATED | : September 18, 2007 |
| INVENTOR(S) | : Martin Arnold et al. |

Page 1 of 1

It is certified that error appears in the above-identified patent and that said Letters Patent is hereby corrected as shown below:

Claim 14, Column 6, Line 1, delete "t oclaim" and insert --to claim--

Signed and Sealed this

Eighteenth Day of December, 2007

JON W. DUDAS
*Director of the United States Patent and Trademark Office*